United States Patent [19]

Macher et al.

[11] Patent Number: 5,831,086
[45] Date of Patent: Nov. 3, 1998

[54] PRODUCTION OF CEFOTAXIME AND NEW SODIUM SALTS

[75] Inventors: Ingolf Macher, Woergl; Gerhard Widschwenter, Soell, both of Austria

[73] Assignee: Biochemie Gesellschaft m.b.H., Kundl, Austria

[21] Appl. No.: 849,974

[22] PCT Filed: Dec. 22, 1995

[86] PCT No.: PCT/EP95/05088

§ 371 Date: Jun. 20, 1997

§ 102(e) Date: Jun. 20, 1997

[87] PCT Pub. No.: WO96/20198

PCT Pub. Date: Jul. 4, 1996

[30] Foreign Application Priority Data

Dec. 23, 1994 [AT] Austria ................................ 2397/94

[51] Int. Cl.$^6$ ................................................. C07D 501/56
[52] U.S. Cl. .......................................................... 540/228
[58] Field of Search ............................................. 540/228

[56] References Cited

U.S. PATENT DOCUMENTS

| | | | |
|---|---|---|---|
| 4,093,803 | 6/1978 | Cook et al. | 544/27 |
| 4,138,555 | 2/1979 | Cook et al. | 544/22 |
| 4,196,205 | 4/1980 | Heymes et al. | 544/28 |
| 4,224,371 | 9/1980 | Amiard et al. | 544/28 |
| 4,680,390 | 7/1987 | Ochiai et al. | 540/222 |
| 4,758,556 | 7/1988 | Dürckheimer et al. | 540/222 |
| 4,973,684 | 11/1990 | Ochiai et al. | 540/222 |
| 5,079,369 | 1/1992 | Takaya et al. | 548/194 |
| 5,574,154 | 11/1996 | Abu-Nasrieh | 540/222 |

FOREIGN PATENT DOCUMENTS

| | | |
|---|---|---|
| 0273156 | 7/1988 | European Pat. Off. . |
| 0347777 | 12/1989 | European Pat. Off. . |
| 2708439 | 7/1978 | Germany . |
| 3539901 | 5/1987 | Germany . |
| 1073530 | 6/1967 | United Kingdom . |
| 9207840 | 5/1992 | WIPO . |

OTHER PUBLICATIONS

Journal of Pharmaceutical Sciences (4 pages) vol. 73, No. 4, Apr. 1984.

Journal of Parenteral Science & Technology (5 pages) vol. 43, No. 2, Mar.–Apr. 1989.

*Primary Examiner*—John M. Ford
*Attorney, Agent, or Firm*—George R. Dohmann

[57] ABSTRACT

A process for the production of cefotaxime in acetone/water and its use in the production of a sodium salt of cefotaxime and a crystalline sodium salt of cefotaxime in the form of rounded agglomerates and in the form of needles.

20 Claims, No Drawings

PRODUCTION OF CEFOTAXIME AND NEW SODIUM SALTS

This invention relates to a process for the production of a cephalosporin, i.e. of—cefotaxime of formula

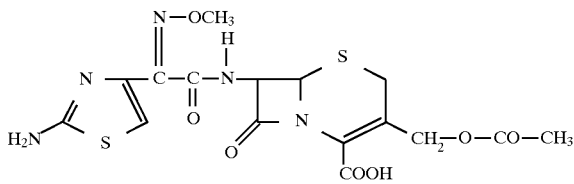

Cefotaxime is a broad spectrum third generation cephalosporin and one of the most important parenterally applied antibiotics. It is generally administered in the form of its sodium salt.

According to processes known in the production of cefotaxime a corresponding side chain in which the amine group may be in protected or unprotected form may be introduced into 7-ACA of formula

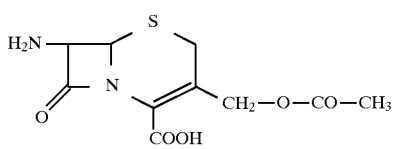

Cefotaxime in the form of the free acid may be converted into the corresponding sodium salt in a further step, using a source of sodium ions.

A highly effective method for introduction of the side chain into 7-ACA is the reaction thereof with a reactive thioester of formula

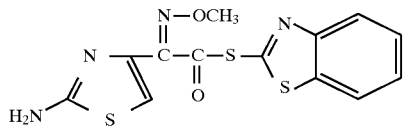

i.e. MAEM.

According to the reaction route described it is not necessary to protect the amine group of the 2-aminothiazolyl function, and the acylation reaction results in high yields without notable secondary reactions. This active ester technology was first described in EP-0 037 380.

According to examples 1 and 2 of EP-0 037 380, the production of cefotaxime in the form of the free acid is carried out by
 a) silylation of 7-ACA of formula II with N,O-bistrimethylsilyl acetamide
 b) acylation of the silylated 7-ACA with MAEM of formula III in dichloromethane
 c) extraction with water/potassium hydrogen carbonate
 d) re-extraction of cefotaxime in the form of the free acid into an ethyl acetate/butanol mixture
 e) drying and evaporation of the organic, cefotaxime-containing phase, and washing with diethylether.

This process is economically feasible, however, dichloromethane is for ecological reasons difficult to use on industrial scale, especially in the production of medicaments and diethyl ether should be avoided for technological safety reasons. Work up of the reaction mixture according to EP-0 037 380 is complicated.

Cefotaxim in the form of the free acid has a high tendency to bind solvents and to form solvates as described for example in U.S. Pat. No. 5,336,776 or in U.S. Pat. No. 4,224,371.

The production of a sodium salt of cefotaxime from a cefotaxime solvate carries along the solvent which corresponds to the solvate into the sodium salt formation step. This results in undesired contamination of the sodium salt with solvents used in the acylation step and in recovery problems of solvents used in the salt formation step.

A simplified, ecologically friendly and economical process for the production of cefotaxim has now surprisingly been found, which overcomes the disadvantages of prior art processes and which provides cefotaxim and the sodium salt thereof in excellent purity, stability and in high yields.

In one aspect the present invention provides a process for the production of a compound of formula

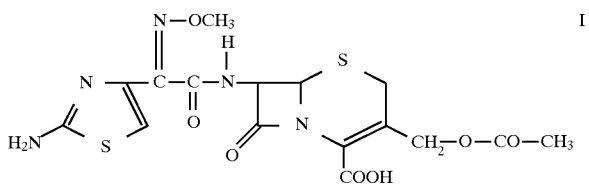

by reacting a compound of formula

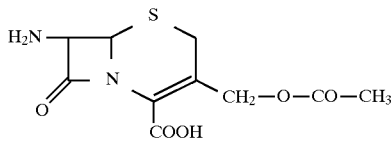

with a compound of formula

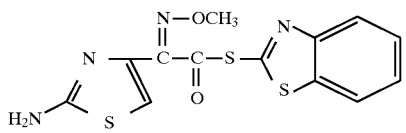

in acetone.

The process of the invention may be carried out as follows:

A compound of formula II is acylated with a compound of formula III using acetone as a solvent. Water may be present. Preferably a mixture of acetone/water is used. The concentration of the reactants in the acylation reaction mixture has generally no influence on the reaction per se. It was, however, surprisingly found that the yields may be dependent on the concentration of the reactants in water and acetone used, although cefotaxime is known to be almost insoluble in water and/or acetone. The yields may decrease with the dilution of the reaction mixture. Thus, the reaction may be carried out in high concentration. Optimal yields may be obtained if per gram of 7-ACA about 3 to 6 ml, for example 3 to 5, e.g. 3.1 to 4.5 ml of acetone and about 0.1 to 0.3, for example 0.1 to 0.25, e.g. 0.13 to 0.18 ml of water are used.

The water:acetone ratio may be such, that a solution is obtained in the presence of a base, for example about 8:1 to about 45:1, e.g. 10:1 to about 35:1. Acylation may be carried as usual.

In one embodiment of the invention 7-ACA of formula II may be suspended in a mixture of acetone and water in the presence of MAEM of formula III and in the presence of a base. Suitable bases include tert.($C_1$–$C_8$)alkyl amines, for example triethylamine, N-ethyl-dimethylamine, a picoline, a N-substituted morpholine; or an inorganic base such as sodium hydroxide, sodium bicarbonate or sodium carbonate or their potassium analogues. The ratio of the base and a compound of formula 2 may be about 1:1 to 1:2; for example 1:1; 1:1.2; 1:1.5. The ratio of a compound of formula III and a compound of formula II may be as described in EP-0 037 380. The temperature is not critical and may be, for example, between 0° and 50° C., e.g. between 10° and 200° C. After termination of the reaction which may be determined as usual, e.g. by chromatography, an acid is added. Suitable acids include an inorganic acid, such as hydrochloric acid, or an organic acid, such as methanesulphonic acid or benzenesulphonic or toluenesulphonic acid. Crystalline cefotaxime is obtained in the form of the free acid of formula I. If desired, e.g. for better stirrability, further acetone or acetone/water mixture may be added to the crystal suspension prior to isolation of cefotaxime.

In another aspect the invention provides the use of a process according to claim 1 in the production of the sodium salt of a compound of formula I as defined in claim 1, e.g. a process for the production of the sodium salt of a compound of formula I as defined in claim 1 comprising i) reacting a compound of formula II with a compound of formula III in acetone ii) converting a compound of formula I obtained in step i) in the presence of a source of sodium ions in acetone.

The compound of formula I obtained in step i) may be isolated.

In a further aspect the invention provides a process for the production of sodium cefotaxime of formula

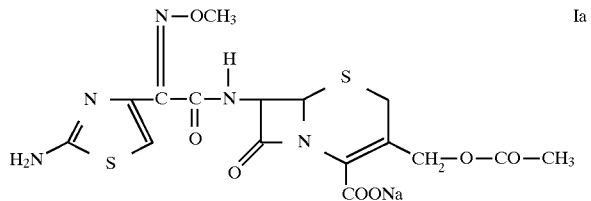

by reacting 7-ACA of formula II with a compound of formula III in a solvent mixture of acetone and water in the presence of a base and converting the compound of formula I as defined in claim 1 into a compound of formula Ia in a solvent mixture of acetone and water in the presence of a source of sodium ions.

The conversion may be carried out in conventional manner. In one embodiment of the invention the conversion is carried out in a solvent as used in the production of the compound of formula I, i.e. cefotaxime in the form of the free acid may be suspended in acetone, e.g. in a mixture of acetone and water, in the presence of a source of sodium ions. The ratio of acetone/water is not critical for the salt formation per se.

A source of sodium ions includes, for example, a sodium salt of a carboxylic acid, such as sodium acetate, a sodium salt of diethylacetic acid or sodium-2-ethyl-hexanoate, or inorganic sources of sodium, such as sodium hydroxide, sodium bicarbonate or sodium carbonate. Sodium ions may be added in an equivalent amount in respect to the carboxylic group of cefotaxime or in an excess, for example in a ratio of 1:1 to 1:2, for example 1:1, or 1:1.5, or 1:1.2. Seed crystals may be added after an optional filtration of the reaction mixture. Further acetone may be added in order to complete crystallization. The reaction temperature is not critical. Crystallisation may be effected, for example at temperatures between 0° and 50° C. To complete crystallisation, the crystal suspension may be further cooled prior to product isolation. Isolation of a sodium salt of cefotaxime may be effected in conventional manner.

Advantages of this process in comparison with EP-0 037 380:

Production of cefotaxime and production of a sodium salt of cefotaxime may be carried out in the same solvent Traces of acetone in a sodium salt of cefotaxime are physiologically acceptable Silylation may be avoided Extraction is omitted.

The process according to the invention is therefore a simple process for the production of a sodium salt of cefotaxime of formula I without protecting group technology and without extraction, i.e. crystallization of cefotaxime may be carried out directly in the reaction vessel. Only a single organic solvent—acetone—is required, which is easy to recover. In addition, cefotaxime and a sodium salt of cefotaxime produced according to the process of the invention are of excellent quality. The process according to the invention is therefore most suitable for use on an industrial scale.

It was surprisingly found that the sodium salt of cefotaxime obtainable according to the process of the invention may be crystallized in form of different (macroscopic) crystals. Primary crystals appear in form of tiny needles. The sodium salt of cefotaxime after termination of crystallisation may be in form of (i) rounded agglomerates (ii) regularly formed needles (iii) a mixture of needles and rounded agglomerates.

The form of the crystals may be dependent on the crystallisation conditions, such as addition time of acetone in the crystallization step (shortened addition time may result in rounded agglomerates), acetone/water ratio (lowering the amount of water may result in rounded agglomerates), amount of seed crystals (lowering the amount of seed crystals may result in a mixture of small needles and small rounded agglomerates), form of seed crystals (the use of needles as seed crystals may unexpectedly result in the sodium salt of cefotaxim in form of rounded agglomerates; the use of prior art crystals, such as e.g. crystals of Claforan® as seed crystals may unexpectedly result in the sodium salt of cefotaxim in form of needles). Under conditions of e.g. example 7, the sodium salt of cefotaxime is obtained substantially in form of rounded agglomerates, and, under conditions of e.g. example 8, the sodium salt of cefotaxime is obtained substantially in form of needles. Crystals of the sodium salt of cefotaxime as known before, e.g. as introduced on the market as the product Claforan®, appear to be a mixture of primary crystals (mainly in form of fragments), which are different from tiny needles, and agglomerates having sharp edges. The crystal form is determined by light microscopy photography.

A sodium salt of cefotaxime in form of rounded agglomerates, or in form of needles, or in form of a mixture of rounded agglomerates and needles is new and advantageous.

The present invention therefore provides in another aspect the sodium salt of cefotaxime, i.e. a sodium salt of a compound of formula I as defined in claim 1, in form of rounded agglomerates and in a further aspect the sodium salt of cefotaxime, i.e. a sodium salt of a compound of formula I as defined in claim 1, in form of needles.

The bulk density of the rounded agglomerates obtainable according to the present invention (determined according to European Pharmacopeia) may vary, e.g. from 0.23 to 0.5 g/ml (Claforan®: 0.46 g/ml). Its tapped density is of, preferably, more than 0.2 g/ml and less than 0.65 g/ml;

more particularly less than 0.6 g/ml, especially less than 0.55 g/ml. The tapped density of the prior art crystals, for example of Claforan®, is of 0.68 g/ml.

Tapped density is determined according to the method given in the European Pharmacopeia after 2500 tappings with a sample of e.g. 10 g. The density rises but plate after ca 2500 tappings.

The present invention provides in another aspect the sodium salt of cefotaxime, i.e. a sodium salt of a compound of formula I as defined in claim 1, in form of rounded agglomerates having a tapped density of 0.2 g/ml to 0.6 g/ml.

The sodium salt of cefotaxime obtainable according to the present invention may be used in the same way and administered in the same dosages and in the same way as the sodium salt of cefotaxime according to prior art.

The sodium salt of cefotaxime in form of rounded agglomerates and in form of needles has a better flowability than crystals according to prior art, for example crystals of Claforan®. Prior art crystals, for example crystals of Claforan®, adhere generally to the wall of a glass container, rounded agglomerates and needles obtainable according to the present invention do not.

In the following examples, which should illustrate the invention more fully without limiting its scope, all temperatures are given in degrees celsius.

Abbreviations:

7-ACA:
  Compound of formula II
MAEM:
  Compound of formula III
Cefotaxime:
  (Z)-(6R,7R)-3-(acetoxymethyl)-7-[2-(2-amino-1,3-thiazol-4-yl)-2-methoxyiminoacetamido]-8-oxo-5-thia-1-azabicyclo[4,2,0]oct-2-en-2-carboxylic acid (compound of formula I)
Sodium salt of cefotaxime:
  (Z)-(6R,7R)-3-(acetoxymethyl)-7-[2-(2-amino- 1,3-thiazol-4-yl)-2-methoxyiminoacetamido]-8-oxo-5-thia-1-azabicyclo[4,2,0]oct-2-en-2-carboxylic acid-sodium salt The content of cefotaxime or of a sodium salt of cefotaxime is determined by HPLC

EXAMPLE 1

Production of cefotaxime 54.4 g of 7-ACA are suspended in a mixture of 20 ml of water and 60 ml of acetone. 30.7 ml of triethylamine are added at room temperature within ca. 10 minutes. A solution is obtained within about 30 minutes. 72.7 g of MAEM are added and a further 120 ml of acetone. After 1.5 hours no further starting material is detected. A total of 18.3 ml of concentrated aqueous hydrochloric acid are added within ca. 10 minutes. After ca. 5 minutes cefotaxime in the form of the free acid crystallizes. The crystal suspension is stirred for 30 minutes at room temperature, and the pH value is adjusted to pH 3.5 using further hydrochloric acid.

400 ml of acetone are added dropwise within 30 minutes, and the mixture is stirred for one hour. Crystalline cefotaxime in the form of the free acid is separated by filtration and dried over night in a vacuum drying chamber.

Yield: 71.6 g; Content of cefotaxime: 93.5%; Residual solvents: acetone 6.2%, water 0.6%

EXAMPLE 2

Production of the sodium salt of cefotaxime 40 g of cefotaxime in free acid form are suspended in a mixture of 40 ml of water and 60 ml of acetone. 12 g of sodium acetate trihydrate are added. A solution is obtained and filtered. The filter bed is washed with a mixture of 3 ml of water and 15 ml of acetone in two portions. 0.4 g of seed crystals are added to the combined filtrates at 25°. The mixture is stirred for one hour. The sodium salt of cefotaxime slowly crystallizes. 600 ml of acetone are added dropwise within 3 hours, and the suspension is stirred for a further 30 minutes at the above temperature. Crystalline sodium salt of cefotaxime is separated by filtration, washed with acetone and dried overnight in a vacuum drying chamber at 40°.

Yield: 36.6 g; Content of the sodium salt of cefotaxime: 95.9%; Water content: 3.8%

EXAMPLE 3

Production of cefotaxime 228.3 g of 7-ACA are suspended in 720 ml of acetone. The suspension is mixed with 30 ml of water, and cooled to 0° to 2°. 112.4 ml of N-ethyldimethylamine are added within ca. 2 minutes. The mixture is stirred at this temperature until a clear solution is obtained (ca. 30 minutes). 296.5 g of MAEM are added, the reaction mixture is warmed to 15° and stirred at this temperature. A solution is obtained after ca. 30 minutes. After 2.5 hours no further starting material is detected. A solution of 207.7 g of p-toluenesulphonic acid monohydrate in 300 ml of acetone is added dropwise within 5 minutes. The reaction mixture is seeded with 1 g of seed crystals and warmed to 20°. The resulting crystal suspension is stirred for another 3 hours at this temperature. Crystalline cefotaxime in the form of the free acid is separated by filtration, washed with acetone and dried in a vacuum drying chamber at 40°.

Yield: 301.0 g; Content of cefotaxime: 91.7%; Residual solvent: acetone 7.8%

EXAMPLE 4

Production of cefotaxime 228.3 g of 7-ACA are suspended in 720 ml of acetone. The suspension is mixed with 30 ml of water, and cooled to 0° to 20°. 134 ml of triethylamine are added within ca. 2 minutes. The mixture is stirred at this temperature, until a clear solution is obtained (ca. 30 minutes). 296.5 g of MAEM are added. The reaction mixture is warmed to 15° and stirred at this temperature. A solution is obtained after ca. 30 minutes. After 4 hours no further staring material is detected. 191.7 g of solid p-toluenesulphonic acid monohydrate is added in portions within ca. 5 minutes. The internal temperature is brought to 20° and the mixture is stirred further. Within ca. 10 minutes the total quantity of p-toluenesulphonic acid goes into solution. 2 g of seed crystals are added to the solution, and stirring is effected for 2 hours at this temperature. The crystal suspension is cooled to 10° and stirred overnight at this temperature. The product is separated by filtration, washed with acetone and dried in a vacuum drying chamber at 40°.

Yield: 341.4 g; Content of cefotaxime: 94.1%; Residual solvents: acetone 6.6%, water 0.5%

EXAMPLE 5

Production of cefotaxime

The reaction is carried out analogously to Example 4 but using 177.2 g of benzenesulphonic acid instead of 191.7 g of p-toluenesulphonic acid monohydrate.

Yield: 308.8 g; Content of cefotaxime: 93.6%; Residual solvents: acetone 7.2%

EXAMPLE 6

Production of cefotaxime

The reaction is carried out analogously to Example 4 but using 92.3 g of methanesulphonic acid instead of 191.7 g of p-toluenesulphonic acid monohydrate.

Yield: 323.9 g; Content of cefotaxime: 93.7%; Residual solvents: acetone 7.7%, water 0.6%

EXAMPLE 7

Production of the sodium salt of cefotaxime 12 g of sodium acetate trihydrate are dissolved in 30 ml of water. 150 ml of acetone and 40 g of cefotaxime in free acid form are added to the stirred solution. A solution is obtained after ca. 10 minutes. The solution is filtered through a filter bed and subsequently through a sterile filter. The filters are washed with a mixture of a total of 6 ml water and 30 ml acetone. The filtrate is brought to 20°, seeded with 0.4 g of seed crystals and stirred for 30 minutes. The sodium salt of cefotaxime partially crystallises. In order to complete crystallisation, 550 ml of acetone are added dropwise within 3 hours, and stirring is effected for a further 30 minutes at 20°. The sodium salt of cefotaxime is separated by filtration, washed with acetone and dried overnight in a vacuum drying chamber at 40°.

Crystalline sodium cefotaxime substantially in form of rounded agglomerates is obtained in flowable form having a tapped density below 0.68 g/ml.

Yield: 38.8 g; Content of the sodium salt of cefotaxime: 95.9%; Residual solvents: acetone 0.4%, water 4.0%

EXAMPLE 8

Production of the sodium salt of cefotaxime 6 g of sodium acetate trihydrate are dissolved in 20 ml of water. 40 ml of acetone and 20 g of cefotaxime in free acid form are added to the stirred solution. The mixture is cooled to 0°. A solution is obtained within 2 to 5 minutes. The solution is filtered through a filter bed and subsequently through a sterile filter. The filters are washed with a chilled mixture of 3 ml of water and 15 ml of acetone. The filtrate is seeded with 0.2 g of seed crystals (Claforan®) and warmed to 20°. The mixture is stirred for 60 minutes. The sodium salt of cefotaxime partially crystallises. In order to compete crystallisation, 300 ml of acetone are added dropwise within 3 hours, and stirring is effected for a further 30 minutes at 20°. The sodium salt of cefotaxime is separated off by filtration, washed with acetone and dried overnight in a vacuum drying chamber at 40° and for 1.5 hours in a stream of dry nitrogen gas at 70°. Crystalline sodium cefotaxime substantially in form of needles is obtained.

Yield: 18.7 g; Content of the sodium salt of cefotaxime: 97.9%; residual solvents: acetone 0.36%, water 1.4%

We claim:

1. A process for the production of a compound of formula I by reacting a compound of formula II with a compound of formula III in acetone.

2. A process according to claim 1 wherein the reaction is carried out in a mixture of acetone and water.

3. A process according to claim 1 wherein a base is present.

4. A process according to claim 1 comprising
  i) reacting a compound of formula II with a compound of formula III in acetone, and
  ii) converting a compound of formula I obtained in step i) into a sodium salt thereof in the presence of a source of sodium ions in acetone.

5. A process according to claim 4 wherein water is present during step i) or ii) or both.

6. A process according to claim 1 for the production of sodium cefotaxime of formula Ia which comprises preparing a compound of formula I by reacting 7-ACA of formula II with a compound of formula III in a solvent mixture of acetone and water in the presence of a base and converting the compound of formula I into a compound of formula Ia as defined above in a solvent mixture of acetone and water in the presence of a sodium source.

7. A process according to claim 1 comprising the steps
  a) reacting a compound of formula II with a compound of formula III in the presence of an inorganic base or a tert.($C_{1-8}$)alkyl amine in an acetone/water mixture
  b) isolating the compound of formula I
  c) reacting a compound of formula I in the presence of a source of sodium ions in an acetone/water mixture, and
  d) isolating the sodium salt of a compound of formula I.

8. A sodium salt of a compound of formula I as defined in claim 1 in form of rounded agglomerates.

9. A sodium salt of a compound of formula I as defined in claim 1 in form of rounded agglomerates having a tapped density of 0.2 g/ml to 0.6 g/ml.

10. A sodium salt of a compound of formula I as defined in claim 1 in form of needles.

11. A process of claim 2 wherein the acetone:water ratio is from 8:1 to 45:1.

12. A process of claim 2 wherein the acetone:water ratio is from 10:1 to 35:1.

13. A process of claim 7 wherein the acetone:water ratio is from 8:1 to 45:1.

14. A process of claim 7 wherein the acetone:water ratio is from 10:1 to 35:1.

15. A process according to claim 6 wherein the compound of formula Ia is isolated in the form of rounded agglomerates.

16. A sodium salt according to claim 8 having a tapped density of 0.2 to 0.6 g/ml.

17. A process according to claim 6 wherein the compound of formula Ia is isolated in the form of needles.

18. A process according to claim 15 wherein the rounded agglomerates have a tapped density of 0.2 to 0.6 g/ml.

19. A process according to claim 2 wherein a base is present.

20. A process according to claim 1 for preparing the sodium salt of the compound of formula I.

* * * * *